United States Patent [19]

Zoche et al.

[11] 4,104,300

[45] Aug. 1, 1978

[54] METHOD OF PREPARING CARBOXYLIC ACID CHLORIDES OF THE BENZENE SERIES

[75] Inventors: Günter Zoche, Bonn-Beuel; Hermann Richtzenhain, Much-Schwellenbach; Wilhelm Vogt, Cologne, all Germany

[73] Assignee: Dynamit Nobel Aktiengesellschaft, Troisdorf, Germany

[21] Appl. No.: 813,595

[22] Filed: Jul. 7, 1977

Related U.S. Application Data

[63] Continuation-in-part of Ser. No. 737,368, Nov. 1, 1976.

[30] Foreign Application Priority Data

Jul. 7, 1976 [DE] Fed. Rep. of Germany ....... 2630429

[51] Int. Cl.$^2$ ............................................. C07C 51/58
[52] U.S. Cl. ............................ 260/544 D; 260/652 R; 260/664
[58] Field of Search ................... 260/544 D; 252/439, 252/441, 443, 467

[56] References Cited

U.S. PATENT DOCUMENTS

| | | | |
|---|---|---|---|
| 2,700,679 | 1/1955 | Carnahan et al. | 260/544 D |
| 3,835,187 | 9/1974 | Dyson | 260/544 D |

FOREIGN PATENT DOCUMENTS

| | | | |
|---|---|---|---|
| 820,698 | 1/1937 | France | 260/544 D |
| 1,954,793 | 5/1971 | Fed. Rep. of Germany | 260/544 D |
| 2,311,825 | 6/1973 | Fed. Rep. of Germany | 260/544 D |

*Primary Examiner*—Gerald A. Schwartz
*Attorney, Agent, or Firm*—Burgess, Dinklage & Sprung

[57] ABSTRACT

In a process for preparing substituted or unsubstituted carboxylic acid chlorides of the benzene series by contacting the corresponding carboxylic acid ester with an aromatic compound containing at least one nuclearly bound trichlormethyl group in the presence of a molybdenum catalyst, the improvement which comprises introducing into the reaction mixture prior to distillation of the carboxylic acid chloride a complexing agent which complexes with the molybdenum catalyst.

11 Claims, No Drawings

METHOD OF PREPARING CARBOXYLIC ACID CHLORIDES OF THE BENZENE SERIES

CROSS-REFERENCE TO RELATED APPLICATION

This is a continuation-in-part of copending application Ser. No. 737,368 filed Nov. 1, 1976 entitled "Process For The Preparation Of Carboxylic Acid Chlorides Of The Benzene Series".

BACKGROUND OF THE INVENTION

1. Field Of The Invention

This invention relates to the process for the preparation of carboxylic acid chlorides of the benzene series. More especially, this invention is directed to an improvement in the preparation of such carboxylic acid chlorides prepared by the use of a molybdenum catalyst, the improvement residing in introducing a complexing agent into the reaction mixture prior to the time that the carboxylic acid chloride is distillatively removed.

2. Discussion Of The Prior Art

In parent application Ser. No. 737,368 there is described a method for the preparation of carboxylic acid chlorides of the benzene series by reaction with the corresponding carboxylic acid ester with an aromatic compound containing at least one nuclearly bound trichlormethyl group in the presence of a molybdenum compound as catalyst. In this reaction it is desirable to remove by distillation from the reaction mixture the alkyl chloride that forms in the reaction and after the end of the reaction to remove the carboxylic acid chloride by distillation, preferably in vacuo.

The acid chlorides which are distilled off contain more or less large quantities of molybdenum. The higher the boiling point of the acid chloride is the higher is the molybdenum content of the distillate and of the desired acid chloride. Thus, it is possible to obtain p-toluylic acid chloride free of molybdenum by distillation while terephthalic acid dichloride obtained by the same process is distilled off in a distillate containing 45 ppm of molybdenum. Similarly, when one attempts to prepare trimellitic acid trichloride by this route employing the molybdenum catalyst the resultant distillate contains 80 ppm of molybdenum. Even when the distillation is performed quite carefully in a column, the molybdenum content is quite high, i.e., is only slightly reduced from those runs performed without the use of a column.

These small quantities of molybdenum in the distillate are undesirable for they necessitate further processing of the carboxylic acid chlorides. In addition, a molybdenum content of more than 40 ppm results in a more or less intense reddish-brown discolored product. Such a product requires extensive further treatment.

It is an object of this invention, therefore, to provide an improved process for the preparation of substituted or unsubstituted carboxylic acid chlorides of the benzene series by reaction of the corresponding carboxylic acid ester with an aromatic compound containing at least one nuclearly bound trichlormethyl group in the presence of a molybdenum catalyst wherein the distillate containing the desired acid chloride product is virtually free of molybdenum. It is another object of this invention to provide such a distilled product wherein the molybdenum content of the distillate is well below 5 ppm.

SUMMARY OF THE INVENTION

In accordance with this invention there is provided an improvement in the process for preparing substituted or unsubstituted carboxylic chlorides of the benzene series by reaction of the corresponding carboxylic acid ester with an aromatic compound containing at least one nuclearly bound trichlormethyl group in the presence of a molybdenum compound as catalyst, the improvement comprising introducing a complexing agent before distillation of the carboxylic acid chloride and thereafter distilling off the carboxylic acid chloride. Through the addition of a complexing agent which complexes with the molybdenum before the distillation, acid chloride distillates are obtained which are virtually free of molybdenum.

In accordance with this invention a complexing agent is introduced into the reaction mixture is a relatively small quantity. Generally speaking, the complexing agent is employed in an amount of 0.1 to 2.5 moles per gram-atom of molybdenum. The amount of complexing agent employed is always related to the amount of molybdenum employed in the process. In principle one can use larger amounts.

The complexing agents can be known complexing agents belonging to entirely different classes of substances. Preferred are organic compounds having oxygen atoms and/or nitrogen atoms having a single pair of electrons. These include, for example, aminocarboxylic acids, iminocarboxylic acids and nitrilocarboxylic acids, such as, for example, ethylenediaminetetraacetic acid or nitrilotriacetic acid.

However, aromatic amines, such as aniline and its derivatives (e.g., terephthalic acid dianilide) or benzamide, are included among the complexing agents which can be used in accordance with the invention.

Also useful are ketones, ethers, or N-heterocyclic compounds. Ketones which are useful include C 4 to C 18 aliphatic ketones, aromatic ketones with i or e nucleus or cycloaliphatic ketones. N-heterocyclic compounds which are useful include those heterocyclics having between 4 and 9 carbocyclic carbon atoms in the ring. Among the ketones, ethers and N-heterocyclic compounds which are contemplated there may be mentioned benzophenone, pyrrolidone-(2), 2,5,8,11,14-pentaoxapentadecane and nicotinic acid. Other ketones, ethers and N-heterocyclic compounds include: acetophenone, acetyl-acetone, acetonyl-acetone, hexanone, pinacoline, di-propylketone, di-butyl-ketone, stearone, mesilyloxide, methyl-vinyl-ketone, divinyl-ketone, cyclohexanone, imidazole, quinoline, nicotinic acid.

Lactams can also be used as complexing agents especially C 5 to C 18 lactams of which $\epsilon$-caprolactam is a typical example.

It is not essential that the required complexing agent be soluble in the reaction mixture. It is added to the reaction mixture prior to the distillation, preferably in substance or dissolved in an appropriate solvent.

The action of the complexing agent takes place independently of whether metallic molybdenum is used as catalyst or a molybdenum compound. The distillates obtained always have molybdenum contents that are lower than 10 ppm of molybdenum. The determination of the molybdenum contents of the distillates was performed by quantitative multi-element analysis by emission spectrography.

In the present method, the same products are used as starting products which are named in Ser. No. 737,368.

Also, the conditions necessary in the reaction between the carboxylic acid esters and the trichlormethyl groups are the same as those given in that patent applicaton.

In addition to metallic molybdenum, virtually all of the known molybdenum compounds can be used as catalyst, such as, for example, the chalcogenides, halides and hydroxyhalides, the carbonyl compounds, or the molybdates. Molybdenum trioxide ($MoO_3$) is used preferentially. Specific molybdenum compounds include:

$MoBr_3$, $MoCl_2$, $MoCl_5$, $MoO_2Cl_2$, $Mo(CO)_6$, $Na_2MoO_4(2H_2O)$, $(NH_4)_6Mo_7O_{24} \cdot 4H_2O$, dioxobis(2,4-pentanedionato-0,0')-molybdenum ($C_{10}H_{14}MoO_6$).

The aromatic carboxylic acid alkyl esters which can be used as starting compounds include esters of mono- and dicarboxylic acids as well as those of tricarboxylic acids, and when dicarboxylic and tricarboxylic acid esters are used the carboxylic acid ester groupings can be in either the ortho or in the meta or para position with respect to one another. The aromatic nucleus can also contain additional substituents, such as $C_{1-18}$ alkyl or alkoxy groups or halogens.

Examples of usable carboxylic acid esters are: toluylic acid methyl esters, toluylic acid ethyl esters, toluylic acid 2-methoxy-ethyl esters, ethylbenzoic acid alkyl esters, chlorobenzoic acid ethyl esters, trichlorobenzoic acid alkyl esters, the alkyl esters of benzoic acid with long alkyl or alkoxy radicals in the nucleus, such as those of dodecylbenzoic acid, dodecoxybenzoic acid or octadecylbenzoic acid. Of the dicarboxylic acid esters we shall mention especially phthalic acid dimethyl ester, isophthalic acid dimethyl ester and terephthalic acid dimethyl ester.

Where reference is made to an alkyl ester preferably the alkyl group has 1–8 carbon atoms, especially 1–4 carbon atoms. Where reference is made to an alkyl group on the nucleus, the alkyl group is 1–18 carbon atoms. The term "long alkyl" refers to $C_{10}$–$C_{18}$ alkyl groups. Where reference is made to "alkoxy" the aklyl group thereof is 1–8 carbon atoms preferably.

The ester grouping can accordingly be based on a monovalent alcohol of 1 to 8 carbon atoms containing, if desired, an oxygen or sulfur atom in the chain. In addition to the esters of mono-, di- and tricarboxylic acids with monovalent alcohols, esters of these carboxylic acids with polyvalent alcohols can also be used. Such esters are, for example, the esters of the aromatic dicarboxylic acids with bivalent alcohols, such as ethylene glycol, propylene glycol, tetramethylene glycol, and cyclohexanedimethanol. Preferred are the polyesters which can be prepared from the above dicarboxylic acids and diols, such as, for example, polypropyleneterephthalate, polytetramethylene isophthalate, polypropylenediphenyldicarboxylate, and poly-1,4-cyclohexanedicarbinolterephthalate. Of special interest here is the recycling of any wastes containing the above-mentioned polyesters.

The trichloromethylbenzenes which can be used as additional starting products include mono, bis and tris-(trichloromethyl) benzenes, which can also be substituted by chlorine. Examples are o-, m- and p-chlorobenzotrichloroides, m- and p-bis(trichloromethyl) benzenes, 1,3-bis-(trichlormethyl)-5-chlorobenzene, the bis-(trichloromethyl) dichlorobenzenes, and o-dichloromethyltrichloromethylbenzene.

The reaction of the invention can be performed without the use of solvents, providing the compounds are fluid at the reaction temperatures. It is also possible, however, to perform it in an inert organic solvent, such as, for example, the chlorobenzenes, toluene, xylene, or diphenyl.

The trichloromethyl component is preferably used in an equimolar ratio to the carboxylic acid ester. Fundamentally one can use a slight excess of up to 10 percent.

One can operate the process at temperatures between 140° and 190° C and obtain within three to four hours yields of more than 90% in the preparation of terephthalic acid chlorides. The amount of catalyst used is considerably smaller than in the known methods. Amounts of 0.1 to 10 grams, and preferably 0.5 to 1.0 grams, per mole of the trichloromethyl group suffice.

The monofunctional acid chlorides that can be prepared by the present process can easily be transformed to the corresponding peroxides, which are used as polymerization catalysts. These acid chlorides can easily be reduced by the Rosenmund reaction to the corresponding aldehydes which are used as intermediates in the preparation of pharmaceuticals (e.g., antibiotics, tranquilizers). Terephthalic acid dichloride and isophthalic acid dichloride are furthermore used for the preparation of polyamides and polyaryl esters of high molecular weight.

The reaction of the benzene carboxylic acid ester with the trichloromethyl containing aromatic compound can be conducted over a broad range of process parameters. Generally speaking the temperature is between 110° and 250° C, preferably between 140° and 190° C. In a preferred embodiment the reaction is conducted at atmospheric pressure at a temperature between 140° and 190° C for between three and four hours.

In order to more fully illustrate the nature of the invention and the manner of practicing the same the following examples are presented.

EXAMPLE 1

A two-liter round flask equipped with thermometer, magnetic stirrer, Vigreux column (40 cm), fractionating column, air condenser and receiver was charged with 777 g (4 moles) of dimethylterephthalate, 1251 g (4 moles) of 1,4-bis-(trichlormethyl)-benzene and 4 g of molybdenum trioxide. The contents of the flask were maintained at 170° to 175° C for 3 hours. The methyl chloride escaping during the reaction was captured in a cold trap following the receiver.

After the end of the reaction, 4 g of finely powdered benzamide was added to the charge. Then terephthalic acid dichloride was obtained by vacuum distillation in a yield of 1559 g and with a purity of 99.8% (GC). The product was colorless and contained less than 3 ppm of molybdenum.

EXAMPLES 2 TO 9

The procedure of Example 1 was followed, except that the complexing agents named in the following table were added instead of benzamide, in the amounts specified in the table.

The terephthalic acid dichloride obtained had the same purity as the product of Example 1. It was colorless and contained less than 3 ppm of molybdenum.

| Complexing agents used in the distillation of terephthalic acid chloride. | | |
| --- | --- | --- |
| Example | Compound | Amount (g) |
| 2 | Benzophenone | 3 |
| 3 | 2,5,8,11,14-pentaoxapentadecane | 5 |
| 4 | Pyrrolidone-(2) | 4 |
| 5 | Aniline | 2 |
| 6 | ε-Caprolactam | 4 |
| 7 | Terephthalic acid dianilide | 4 |
| 8 | Ethylenediaminetetraacetic acid | 4 |
| 9 | Nicotinic acid | 1 |

Example for Purposes of Comparison

Example 1 was repeated, except that no complexing agent was added prior to the distillation of the terephthalic acid dichloride.

The terephthalic acid dichloride obtained was of a reddish brown color and had a molybdenum content of 45 ppm.

What is claimed is:

1. In a process for preparing a substituted or unsubstituted carboxylic acid chloride of the benzene series by reaction of the corresponding carboxylic acid ester with an aromatic compound containing at least one nuclearly bound trichlormethyl group in the presence molybdenum or a molybdenum compound as catalyst wherein the corresponding carboxylic acid chloride is recovered by distillation, the improvement which comprises introducing into the reaction product prior to distillation of the carboxylic acid chloride a complexing agent which complexes with the molybdenum or molybdenum containing catalyst.

2. A process according to claim 1 wherein the complexing agent is added in an amount between 0.1 and 2.5 moles per gram atom of molybdenum.

3. A process according to claim 1 wherein the complexing agent is benzamide.

4. A process according to claim 1 wherein the complexing agent is benzophenone.

5. A process according to claim 1 wherein the complexing agent is 2,5,8,11,14-pentaoxapentadecane.

6. A process according to claim 1 wherein the complexing agent is pyrrolidone-(1).

7. a process according to claim 1 wherein the complexing agent is aniline.

8. A process according to claim 1 wherein the complexing agent is ε-caprolactam.

9. A process according to claim 1 wherein the complexing agent is terephthalic acid dianilide.

10. A process according to claim 1 wherein the complexing agent is ethylenediaminetetraacetic acid.

11. A process according to claim 1 wherein the complexing agent is nicotinic acid.

* * * * *